United States Patent
Reeves (10) Patent No.: US 11,471,589 B2
(45) Date of Patent: Oct. 18, 2022

(54) AUTOMATIC FLUID PRODUCT INJECTION DEVICE

(71) Applicant: APTAR FRANCE SAS, Le Neubourg (FR)

(72) Inventor: Sam Reeves, Bristol (GB)

(73) Assignee: APTAR FRANCE SAS, Le Neubourg (FR)

(*) Notice: Subject to any disclaimer, the term of this patent is extended or adjusted under 35 U.S.C. 154(b) by 183 days.

(21) Appl. No.: 16/607,879

(22) PCT Filed: Apr. 23, 2018

(86) PCT No.: PCT/FR2018/051010
§ 371 (c)(1),
(2) Date: Oct. 24, 2019

(87) PCT Pub. No.: WO2018/197792
PCT Pub. Date: Nov. 1, 2018

(65) Prior Publication Data
US 2020/0061285 A1    Feb. 27, 2020

(30) Foreign Application Priority Data

Apr. 26, 2017  (FR) ..................................... 1753611

(51) Int. Cl.
*A61M 5/14*     (2006.01)
*A61M 5/145*    (2006.01)

(52) U.S. Cl.
CPC ........ *A61M 5/1408* (2013.01); *A61M 5/1454* (2013.01); *A61M 2005/14506* (2013.01); *A61M 2205/8206* (2013.01)

(58) Field of Classification Search
CPC ............ A61M 5/14248; A61M 5/1408; A61M 5/1454; A61M 5/3146; A61M 2005/14252; A61M 2005/14506
See application file for complete search history.

(56) References Cited

U.S. PATENT DOCUMENTS

2002/0040208 A1* 4/2002 Flaherty ............ A61M 5/14248
604/288.01
2004/0092877 A1* 5/2004 Langley ............ A61M 5/31511
604/151

(Continued)

FOREIGN PATENT DOCUMENTS

GB   2 434 548 A     8/2007
WO   02/40083 A2     5/2002

(Continued)

OTHER PUBLICATIONS

International Search Report for PCT/FR2018/051010 dated Aug. 21, 2018 (PCT/ISA/210).

*Primary Examiner* — James D Ponton
(74) *Attorney, Agent, or Firm* — Sughrue Mion, PLLC (57) ABSTRACT

An automatic fluid injection device having an upper body (1) with an injection system (3, 4, 5) controlled by a power supply (7) and that is triggered by a user interface (100); and an insertion mechanism (8, 9) for inserting an injection needle (110); a base body (2) for coming into contact with an injection zone and having a fluid reservoir (6) containing an injection piston (65), and a needle assembly (10) including the injection needle (110). The injection system has an elongated spring metal strip (3) wound on a respective reel (30) before actuation; and a drive mechanism (5) for unwinding the strip (3) against a respective piston (65) so as to perform the injection, and for rewinding the strip (3) on the reel (30) after injection.

20 Claims, 6 Drawing Sheets

(56) References Cited

U.S. PATENT DOCUMENTS

| | | | | |
|---|---|---|---|---|
| 2005/0277912 A1* | 12/2005 | John | .................. | G16H 20/17 |
| | | | | 604/890.1 |
| 2012/0172804 A1* | 7/2012 | Plumptre | .......... | A61M 5/14566 |
| | | | | 604/154 |
| 2015/0209505 A1* | 7/2015 | Hanson | ............. | A61M 5/14546 |
| | | | | 604/135 |

FOREIGN PATENT DOCUMENTS

| | | |
|---|---|---|
| WO | 03/090509 A2 | 11/2003 |
| WO | 2013/016376 A2 | 1/2013 |

\* cited by examiner

AUTOMATIC FLUID PRODUCT INJECTION DEVICE

CROSS REFERENCE TO RELATED APPLICATIONS

This application is a National Stage of International Application No. PCT/FR2018/051010 filed Apr. 23, 2018, claiming priority based on French Patent Application No. 1753611 filed Apr. 26, 2017.

The present invention relates to an automatic fluid injection device.

Automatic fluid injection devices are well known. In particular, they include autoinjectors in which the contents of a reservoir, generally a syringe, are automatically injected by means of an actuator system that generally includes a loaded spring, and that, on being triggering, moves a piston in the reservoir so as to inject the fluid.

Such prior-art devices can present problems, in particular when the volumes to be dispensed are large, when the fluid is relatively viscous, or when a plurality of fluids need to be combined in a single treatment.

Document WO 02/40083 describes a dispenser in accordance with the preamble of claim 1.

An object of the present invention is to provide an automatic injection device that does not have the above-mentioned drawbacks.

Another object of the present invention is to provide an automatic injection device that makes it possible to dispense fluid automatically, even at large volumes and/or high viscosities.

Another object of the present invention is to provide an automatic fluid injection device that is simple and inexpensive to manufacture and to assemble.

The present invention thus provides an automatic fluid injection device comprising:
  an upper body comprising: at least one injection system that is controlled by power supply means and that is triggered by a user interface, such as at least one actuator button; and an insertion mechanism for inserting an injection needle; and
  a base body for coming into contact with an injection zone and comprising: at least one fluid
  †Translation of the title as established ex officio. reservoir, each containing an injection piston; and a needle assembly including said injection needle;
  wherein said injection system comprises:
  at least one elongate spring metal strip, each strip being wound on a respective reel before actuation; and
  a drive mechanism for unwinding said at least one strip against a respective piston so as to perform the injection, and for rewinding said strip on said reel after injection.

Advantageously, in its unwound state, said strip is curved along its longitudinal axis.

Advantageously, each strip is delivered via a guide so that the free end of said strip is in its correct position for engaging with said piston of the respective reservoir.

Advantageously, said drive mechanism comprises an electric motor and a worm gear drive.

Advantageously, said insertion mechanism comprises an insertion actuator and needle movement means, such as a plunger.

Advantageously, said base body includes a dispenser pipe, including a respective priming needle for each reservoir.

Advantageously, the device includes means for priming said device while assembling said upper body on said base body.

Advantageously, the device includes means for guaranteeing that said insertion mechanism can be actuated in order to insert the injection needle into the injection zone after priming.

Advantageously, the device includes means for guaranteeing that said injection system can be actuated only after the injection needle has penetrated into the injection zone.

Advantageously, the device includes means for guaranteeing that said insertion mechanism can be actuated in order to retract the injection needle out from the injection zone only after the end of injection.

Advantageously, including mechanical and/or software verification means for determining the end of injection, in particular verification means for verifying the turning of a reel.

Advantageously, said base body includes a sticker for fastening onto the injection zone.

Advantageously, said base body includes at least two reservoirs, in particular three reservoirs.

Advantageously, each reservoir has a fluid content in the range 1 milliliters (mL) to 10 mL, advantageously about 3 mL.

Advantageously, said power supply means comprise an optionally rechargeable battery.

These characteristics and advantages and others appear more clearly from the following detailed description, given by way of non-limiting example, and with reference to the accompanying drawings, in which.

The invention relates to an automatic injection device that is particularly adapted to dispense relatively large volumes of fluid, typically of the order of a few milliliters, typically in the range 1 mL to 10 mL, e.g. 3 mL. The device of the invention is also adapted to dispense fluids that are relatively viscous.

The device comprises two distinct portions.

The base body 2 contains: the medication reservoir(s) 6, each provided with an injection piston 65 and with a closure membrane or septum 61; the needle assembly 10, including an injection needle 110; and a dispenser pipe 11, including a respective priming needle 111 for each reservoir 6, said dispenser pipe 11 connecting each reservoir 6 to said needle assembly 10. Said base body 2 is preferably disposable.

The upper body 1 contains: the injection system 3, 4, 5; the power supply 7; the insertion mechanism 8, 9 for inserting the injection needle 110; and the user interface 100, in particular an actuator button. The upper body 1 may be disposable, but preferably it is reusable. In particular, it is possible to envisage that various upper bodies 1, e.g. adapted for different users, are capable of co-operating with a single base body 2.

Advantageously, the device is presented to the user with the medication reservoir(s) 6 pre-assembled in the base body 2.

In use it is possible to perform the following steps:

1) The user removes the packaging and assembles together the two portions of the apparatus, namely the upper body 1 and the base body 2;

2) The user removes the sticker support from the base body and fastens the device on the injection site;

3) The user actuates the device, in particular via the actuator button 100, so as to cause the needle 110 to be inserted, the injection to be performed, and the needle 110 to be retracted;

4) When the injection process has ended, the user removes the device from the injection site.

5) The user separates the two portions of the apparatus and preferably disposes of the base body only.

Figure 1:
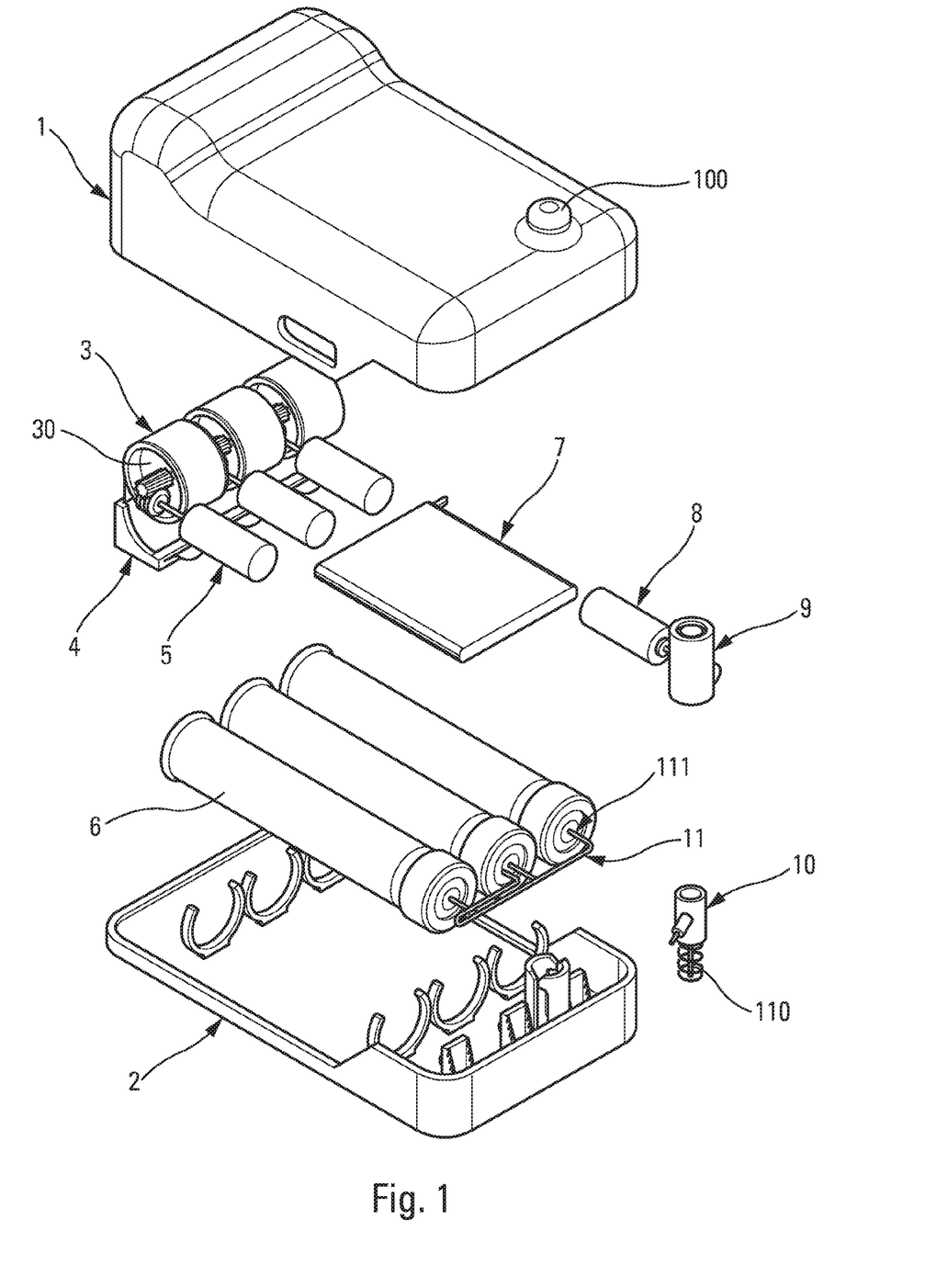
FIG. 1 is an exploded diagrammatic perspective view of an automatic injection device in an advantageous embodiment.
Figure 2:
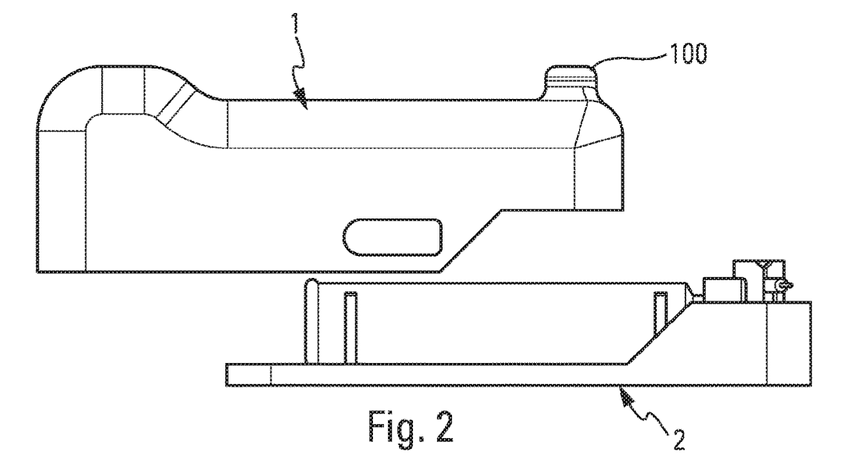
FIG. 2 is a diagrammatic side view of the FIG. 1 device.

FIGS. 1 and 2 show an automatic injection device in an advantageous embodiment.

In the embodiment shown, the power supply 7 is an optionally rechargeable battery.

Before using the apparatus, the patient must assemble together the upper body 1 and the base body 2 of the apparatus.

This causes the reservoirs 6 to be moved in said base body 2 relative to the priming needles 111, which needles remain stationary in the base body 2 during assembly. In this way, each priming needle 111 pierces the septum 61 of a respective reservoir 6. Thus, when the two portions of the apparatus are assembled together, said apparatus is primed and ready to use.

Figure 3:
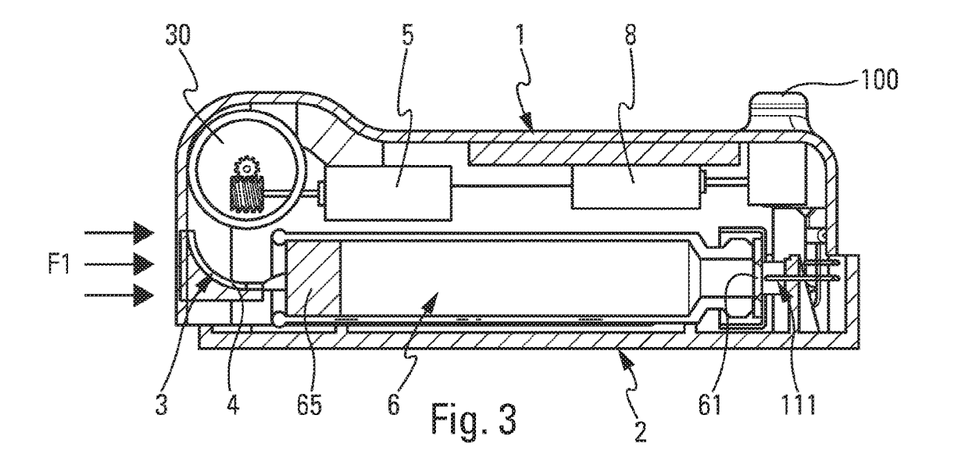
FIGS. 3 and 4 are diagrammatic section views of the device in FIGS. 1 and 2, respectively before and after priming.
Figure 4:
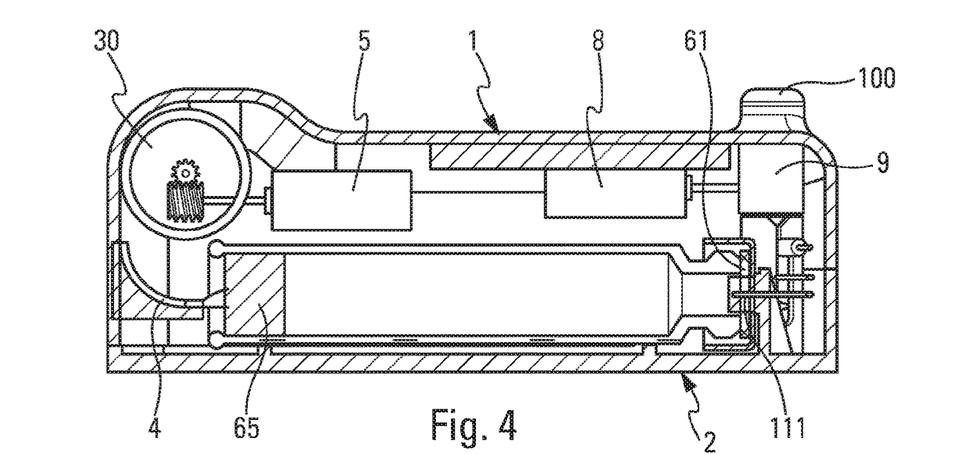
Figure 5:
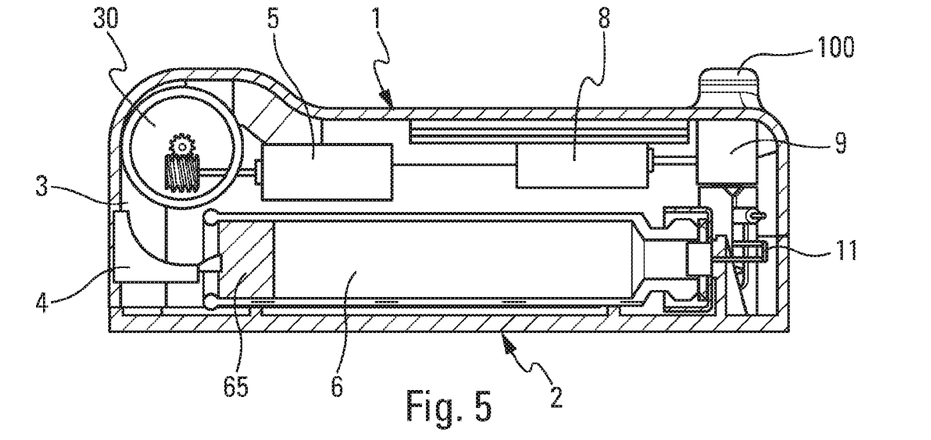
FIGS. 5 to 7 are diagrammatic section views of the device in FIGS. 1 and 2, respectively before injection, after injection, and after retracting the injection needle.

More precisely, the reservoir(s) 6 and the needle assembly 10 are housed in the base body 2 of the device. In the state prior to assembly, the reservoirs 6 are in a retracted position relative to the priming needles 111 and the septums 61 are intact. When the upper body 1 and the base body 2 are assembled together, a strip drive-mechanism 3, forming part of the injector system, is engaged with the rear of each reservoir 6. During assembly, the upper body 6 slides laterally (towards the right in the example in FIGS. 3 and 4, as shown by arrows F1) relative to the base body 2 in order to be locked in place. In this way, the reservoirs 6 are thrust against the priming needles 111 and the septums 61 are pierced.

When a plurality of reservoirs 6 are used, as shown in the example in the figures, the priming needles 111 of all of the reservoirs 6 are coupled to a single injection needle 110.

The embodiment described presents the particular advantage that it enables disposable components and reusable components to be combined. The components that come into contact with the medication are housed in the base body 2 and are disposable. The components of the injection system, the insertion system for inserting the injection needle, and the user interface are housed in the upper body 1, and can thus be reusable.

The injection needle 110 is inserted into the injection site by means of an insertion actuator 8, in particular a mechanical actuator, acting on a needle plunger 9, and is retracted by means of a return spring 12. In a variant, the insertion actuator 8 could be an electromechanical actuator, e.g. comprising a motor associated with a worm screw. Other variants may also be envisaged.

Preferably, means are provided for guaranteeing that the injection needle 110 can be deployed only after the device has been primed. This can be identified by mechanical and/or software verification, e.g. by verifying the relative position of the upper body 1 and of the base body 2. For example, when both bodies 1, 2 are assembled together in order to prime the apparatus, the plunger 9 of the injection needle 110 comes into alignment with the needle assembly 10; consequently, the needle 110 cannot be deployed before priming.

Figure 6:
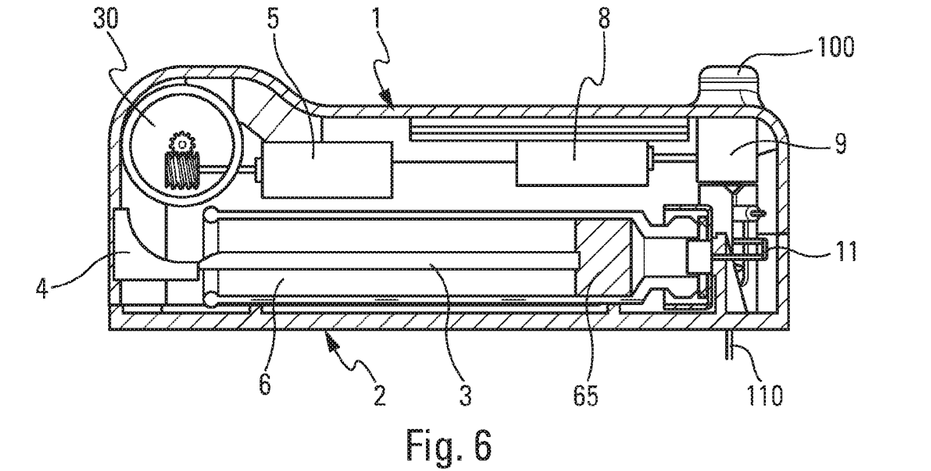
Figure 12:
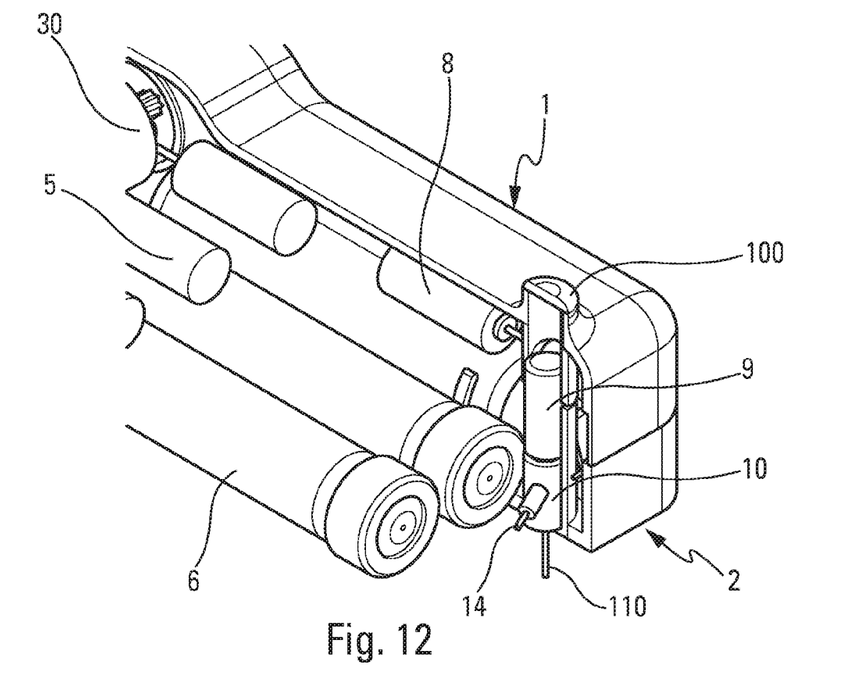

When the device is actuated, e.g. via the actuator button 100, the insertion actuator 8 presses down the plunger 9 which, in turn, drives the injection needle 110 into the injection site, as can be seen in FIGS. 6 and 12.

Figure 7:
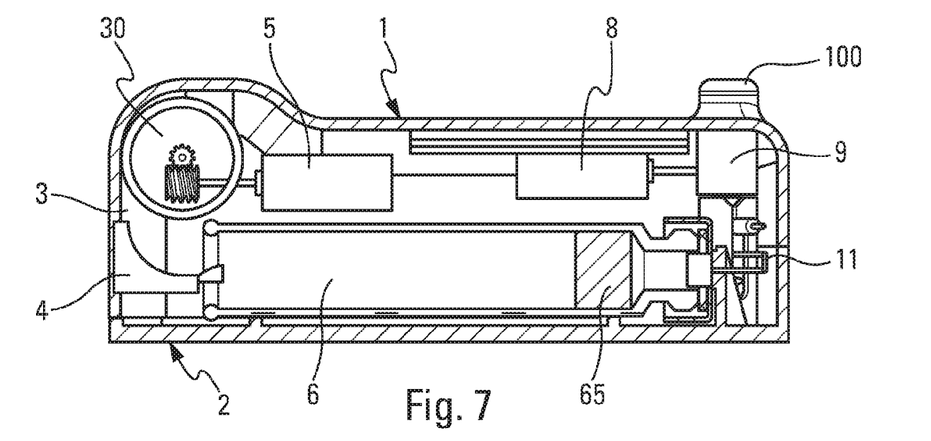
Figure 8:
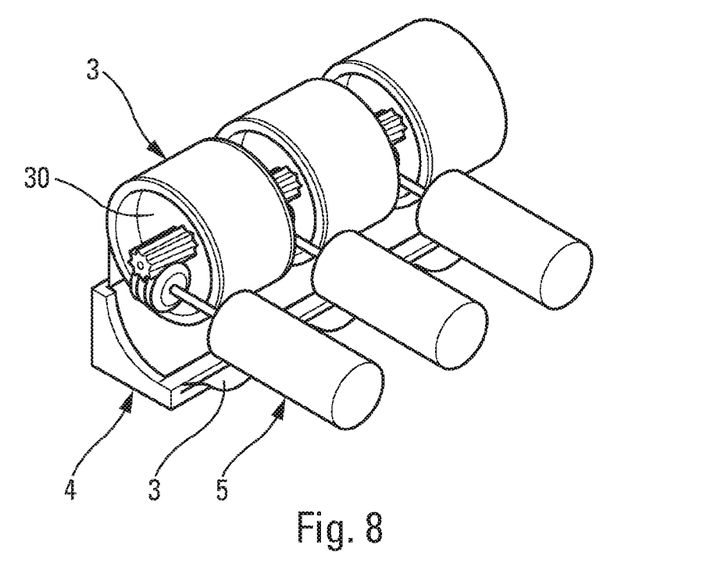
FIGS. 8 and 9 are diagrammatic perspective views of a detail of an injection mechanism in an advantageous embodiment, respectively before and after injection.
Figure 13:
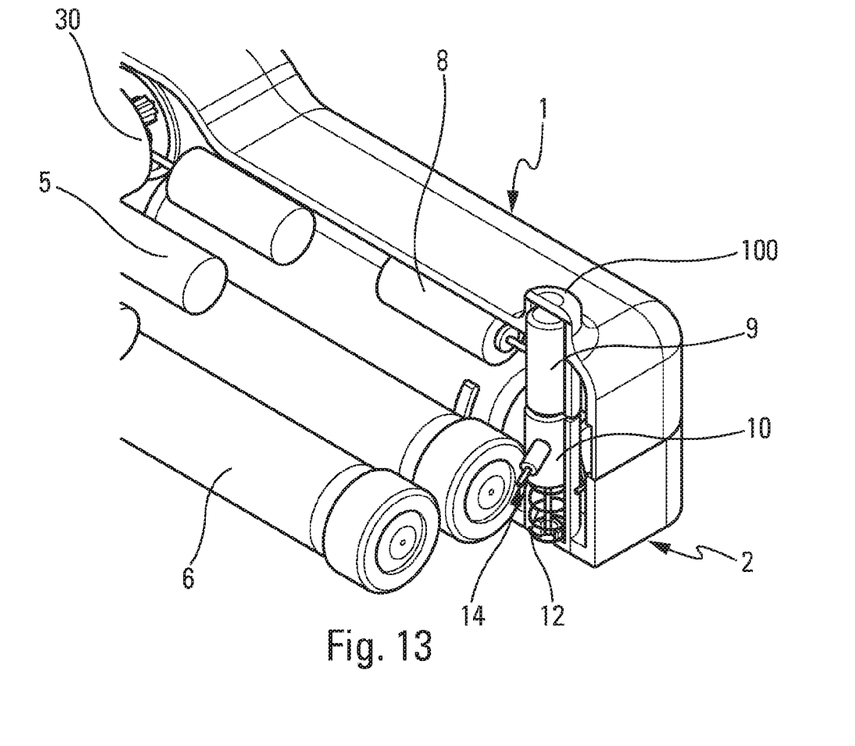

When injection has terminated, the insertion actuator 8 retracts the plunger 9, and the return spring 12 removes the needle from the injection site, as can be seen in FIGS. 7 and 13. The end of injection may be identified by mechanical and/or software verification means, e.g. monitoring the turning of a reel 30 carrying a strip 3.

The embodiment described presents, in particular, the advantage that the mechanical components of the insertion mechanism are separate from the components of the needle assembly 10 that enter into contact with the patient and/or the medication. This enables the insertion mechanism to be reusable.

The injection system includes at least one elongate strip of spring metal, typically made out of spring steel. In its free form, i.e. when it is not wound on a reel, the strip 3 is curved along its longitudinal axis so as to create a certain degree of stiffness. When it is flat, the strip 3 can be wound on a reel 30 so as to occupy a small volume during storage.

The device may include one or more strips 3 for dispensing the contents of one or more reservoirs.

Each strip 3 is delivered via a guide 4 so that the free end of the strip 3 is in its correct position for engaging with the piston 65 of the respective reservoir 6.

During the injection process, the strip reels 30 are turned by means of a drive mechanism 5. In the embodiment shown, said drive mechanism comprises an electric motor and a worm gear drive. Other appropriate variants may also be envisaged.

Figure 9:
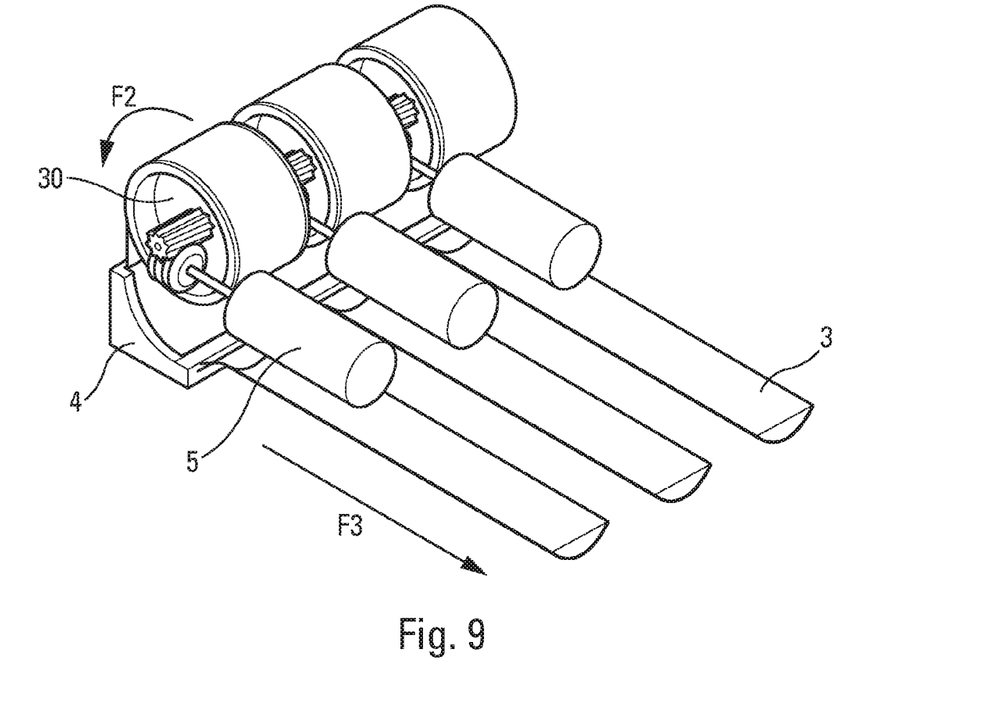
Figure 10:
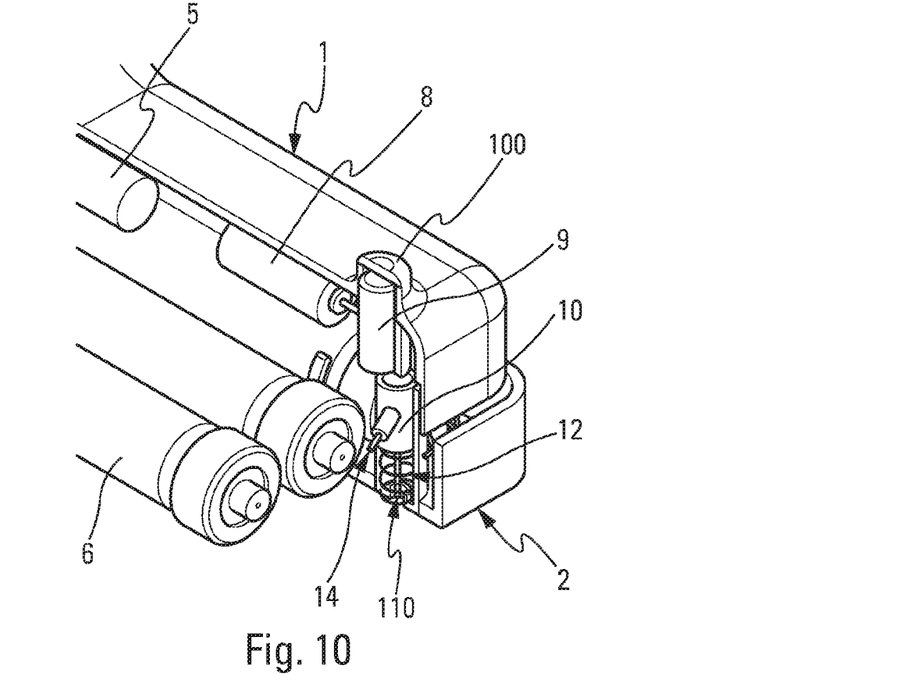
FIGS. 10 to 13 are diagrammatic side views of the needle assembly, respectively before priming, before pricking, after injection, and after retracting the needle.
Figure 11:
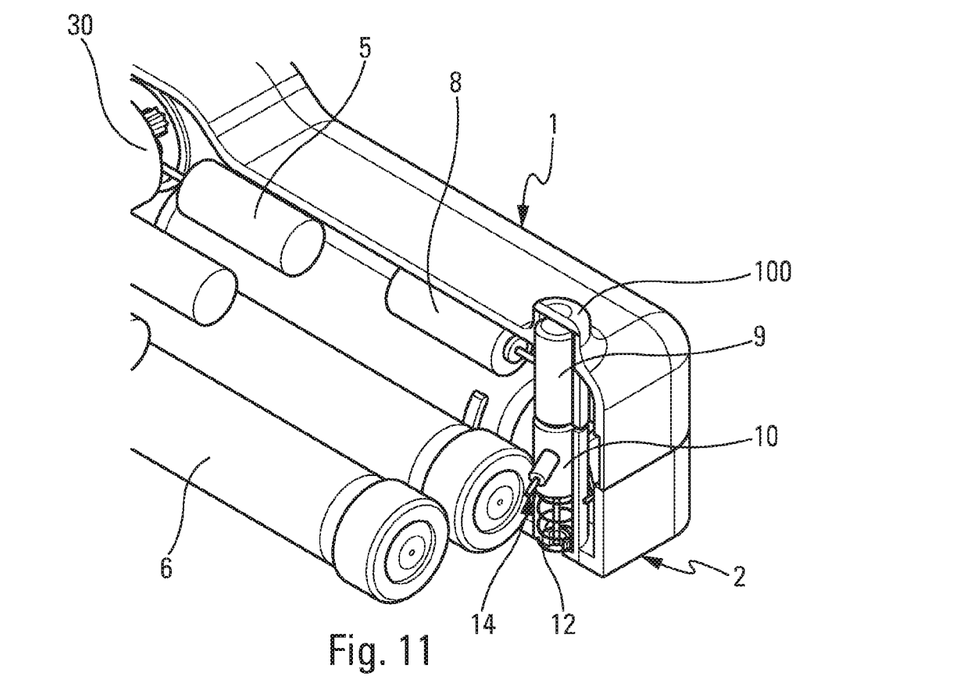

When the strip reel 30 turns, as shown by arrow F2 in FIG. 9, the strip 3 is forced into the guide 4 and against the piston 65 of the reservoir 6. When the strip 3 leaves the guide, it returns to its curved shape, as can be seen in FIG. 9. This creates a length of strip that is substantially rigid and that is adapted to push the piston 65 of the reservoir 6, as shown by arrow F3.

When the injection of the medication(s) has terminated, the drive mechanism 5 is reversed and the strip 3 is retracted, thus being rewound on its reel 30.

The embodiment described presents the particular advantage that the injection system is reversible and thus reusable. Furthermore, it presents a shape that is compact as a result of the strip(s) 3 being wound flat on the reel(s) 30.

Advantageously, the drive mechanism 5 of the injection system can be actuated only after the injection needle 110 has penetrated into the injection site. This may be achieved by means of mechanical and/or software verification, e.g. by analyzing the position of the plunger 9 of the insertion mechanism for inserting the needle.

The device shown in the figures includes three injection systems that act on three reservoirs 6. The three injection systems may be actuated simultaneously by means of a single actuator button 100 so as to dispense the contents of all three reservoirs simultaneously, which contents are thus mixed together upstream of the injection needle 110. In a variant, the three injection systems may be actuated in succession so as to dispense the contents of the three reservoirs successively. The successive actuations may be triggered by means of separate actuator buttons, but provision could also be made for a single actuator button that automatically triggers the dispensing sequence. A combination of these two variants is also possible, e.g. dispensing in two stages, i.e. firstly dispensing the contents of one reservoir, and secondly dispensing a mixture from the other two reservoirs simultaneously.

The above-described embodiment provides the following advantages in particular:
  the speed of injecting the fluid may be adjusted so as to optimize individual treatments, and it may also vary over time; and
  the injection systems and the multiple reservoirs make it possible to use a combination of medications that may be dispensed at different speeds and at different moments.

The use of a device having one or more reservoirs makes it possible in particular to provide the following advantages:
  a single device for two or more types of fluid, which may require different volumes to be dispensed;
  the possibility of dispensing cocktails or a mixture of two or more fluids;
  the possibility of associating pain-reducing agents (anesthetics, acid neutralizers, etc.) together with the medication to be injected;
  the possibility of having different medication treatment frequencies; e.g. a first sequence S1 of taking a plurality of different medications, followed by a second sequence S2 of taking a single medication, etc.;
  the possibility of standardizing the injection device for several types of treatment;
  a reduction in the cost of developing devices;
  the possibility of adjusting the formulation of the fluid;
  various fluid formulations may be housed in a single device; and
  a reduction in the number of injections.

The present invention is described above with reference to an advantageous embodiment, but naturally any modification could be applied thereto by the person skilled in the art, without going beyond the ambit of the present invention, as defined by the accompanying claims.

The invention claimed is:

1. An automatic fluid injection device comprising:
  an upper body comprising: at least one injection system that is controlled by power supply means and that is triggered by a user interface; and an insertion mechanism for inserting an injection needle; and
  a base body for coming into contact with an injection zone and comprising: at least one fluid reservoir, each containing an injection piston; and a needle assembly including said injection needle;
  wherein said injection system comprises:
  at least one strip in the form of a metal spring, each of said at least one strip wound on a respective reel before actuation; and
  a drive mechanism for unwinding said at least one strip against a respective piston so as to perform an injection, and for rewinding said at least one strip on said reel after the injection, and
  wherein, in an unwound state, said at least one strip is curved along a longitudinal axis of the at least one strip so as to create stiffness in said at least one strip.

2. The device according to claim 1, wherein each of said at least one strip is delivered via a guide so that a free end of said at least one strip is in a correct position for engaging with said piston of a respective one of the at least one fluid reservoir.

3. The device according to claim 1, wherein said drive mechanism comprises an electric motor and a worm gear drive.

4. The device according to claim 1, wherein said insertion mechanism comprises an insertion actuator and needle movement means.

5. The device according to claim 4, wherein the needle movement means is a plunger.

6. The device according to claim 1, wherein said base body includes a dispenser pipe, including a respective priming needle for each reservoir of the at least one fluid reservoir.

7. The device according to claim 6, including means for priming said device while assembling said upper body on said base body.

8. The device according to claim 1, including means for guaranteeing that said insertion mechanism can be actuated in order to insert the injection needle into the injection zone after priming.

9. The device according to claim 1, including means for guaranteeing that said injection system can be actuated only after the injection needle has penetrated into the injection zone.

10. The device according to claim 1, wherein said insertion mechanism retracts the injection needle out from the injection zone only after an end of injection.

11. The device according to claim 10, including mechanical and/or software verification means for determining the end of injection.

12. The device according to claim 10, including mechanical and/or software means for verifying turning of a reel.

13. The device according to claim 1, wherein said base body includes a sticker for fastening onto the injection zone.

14. The device according to claim 1, wherein said at least one fluid reservoir comprises at least two reservoirs.

15. The device according to claim 1, wherein each reservoir of the at least one fluid reservoir has a fluid content in range 1 mL to 10 mL.

16. The device according to claim 1, wherein said power supply means comprises a rechargeable battery.

17. The device according to claim 1, wherein during unwinding, said at least one strip is forced against a respective piston to push said piston.

18. The device according to claim 1, wherein the user interface is at least one actuator button.

19. The device according to claim 1, wherein said at least one fluid reservoir comprises three reservoirs.

20. The device according to claim 1, wherein each reservoir of the at least one fluid reservoir has a fluid volume of about 3 mL.

* * * * *